US012797401B2

(12) United States Patent
Lu et al.

(10) Patent No.: US 12,797,401 B2
(45) Date of Patent: Nov. 17, 2026

(54) USE OF BAICALIN IN PREPARATION OF ANTI-PSEUDORABIES VIRUS MEDICAMENT

(71) Applicant: KEY LABORATORY OF ANIMAL IMMUNOLOGY, HAAS, Zhengzhou City (CN)

(72) Inventors: Qingxia Lu, Zhengzhou City (CN); Zhenhua Guo, Zhengzhou City (CN); Maoyang Weng, Zhengzhou City (CN); Qiaoge Niu, Zhengzhou City (CN); Qianyue Jin, Zhengzhou City (CN); Yao Jiang, Zhengzhou City (CN); Jifei Yang, Zhengzhou City (CN); Weitao Xie, Zhengzhou City (CN); Fengxia Lv, Zhengzhou City (CN); Lingjuan Li, Zhengzhou City (CN)

(73) Assignee: Key Laboratory of Animal Immunology, HAAS, Zhengzhou City (CN)

( * ) Notice: Subject to any disclaimer, the term of this patent is extended or adjusted under 35 U.S.C. 154(b) by 454 days.

(21) Appl. No.: 18/378,310

(22) Filed: Oct. 10, 2023

(65) Prior Publication Data

US 2024/0156847 A1 May 16, 2024

(30) Foreign Application Priority Data

Oct. 31, 2022 (CN) ......................... 202211344439.7

(51) Int. Cl.
*A61K 31/7048* (2006.01)
*A61P 31/22* (2006.01)

(52) U.S. Cl.
CPC .......... *A61K 31/7048* (2013.01); *A61P 31/22* (2018.01)

(58) Field of Classification Search
CPC .................................................. A61K 31/7048
See application file for complete search history.

(56) References Cited

FOREIGN PATENT DOCUMENTS

CN 104666324 A 6/2015

OTHER PUBLICATIONS

Shen, European Journal of Pharmacology 465 (2003) 171-181. (Year: 2003).*
Green, Expert Opinion of Drug Discovery, 3:6, 671-676, 2008. (Year: 2008).*
Jinzhou Jingliang Animal Pharmaceutical Co., Ltd., "Antiphlogistic Powder of Schizonepetae and Ledebouriellae", Released Jan. 20, 2022, 4 pages.

* cited by examiner

*Primary Examiner* — Layla D Berry
(74) *Attorney, Agent, or Firm* — Moore & Van Allen PLLC

(57) ABSTRACT

Use of baicalin in preparation of a medicament for resisting pseudorabies virus (PRV) and diseases caused thereby is provided. The present disclosure relates to the technical field of medicine. It is found for the first time in the present disclosure that the baicalin has anti-PRV activity, has no obvious toxicity to cells in the using concentration range of 31.25-125 μM, and shows an obvious inhibitory effect on PRV replication and proliferation in the concentration range of 62.5-125 μM. It can be foreseen that the baicalin can be developed as a safe and effective anti-PRV medicament, and a novel anti-PRV medicament under existing application conditions of the baicalin, with an excellent application prospect.

2 Claims, 3 Drawing Sheets

USE OF BAICALIN IN PREPARATION OF ANTI-PSEUDORABIES VIRUS MEDICAMENT

CROSS REFERENCE TO RELATED APPLICATION

This patent application claims the benefit and priority of Chinese Patent Application No. 202211344439.7, filed with the China National Intellectual Property Administration on Oct. 31, 2022, the disclosure of which is incorporated by reference herein in its entirety as part of the present application.

TECHNICAL FIELD

The present disclosure relates to use of baicalin in preparation of an anti-pseudorabies virus (PRV) medicament, and belongs to the technical field of biomedicine.

BACKGROUND

Pseudorabies virus (PRV) is an enveloped double-stranded DNA virus with a genome size of approximately 140 kb, encoding at least 70 proteins. PRV belongs to genus Varicellovirus of the subfamily Alphaherpesvirinae. Pigs are the only natural host of PRV. The disease caused by PRV infection in pigs is called pseudorabies. The common clinical manifestations include reproductive disorders in sows, neurological symptoms in piglets, and respiratory tract symptoms in nursery and fattening pigs. Pseudorabies is a viral disease which is harmful to the pig industry in China and one of the diseases that need to be eradicated in breeding pig farms. In addition, PRV can further infect a plurality of animals, like dogs, cats, cattle, sheep, foxes, minks and wolves, and has a wide spectrum of infection. Except for pigs, most other animals die within 24-48 hours after infection.

Since 2011, due to the emergence of PRV variant strains in China, PRV has been pandemic in pigs again. The PRV epidemic has seriously restricted the production efficiency and development of pig industry in China. In addition, since 2018, several cases of PRV infection in humans have been reported in China, suggesting that PRV has the risk of interspecies transmission under certain conditions. Therefore, PRV poses a threat to pig breeders and public health. Currently, there is no effective drug for treating the PRV infection.

*Scutellaria baicalensis* is a perennial herbaceous plant of the genus *Scutellaria* of the family Labiatae, which has been used medicinally in China for more than 2,000 years. According to traditional Chinese medicine (TCM) theory, Scutellariae Radix has the functions of clearing heat and promoting diuresis, and clearing fire and detoxifying. Modern pharmacological studies have found that Scutellariae Radix has the functions of protecting the nervous system, immune system and liver, and further has anti-tumor, anti-oxidative and anti-pathogenic microbial infection activity. Scutellariae Radix mainly exerts pharmacological effects thereof through a plurality of flavonoid compounds contained therein. Herein, pharmacological effects of baicalin as one of the important flavonoid active ingredients of Scutellariae Radix have been widely studied. Baicalin shows excellent potential for clinical application in terms of the treatment of inflammation and cancers and antiviral action, but there is no application report of baicalin resisting PRV.

BRIEF SUMMARY

Aiming at the deficiencies of the prior art, the present disclosure aims to provide use of baicalin in preparation of an anti-PRV medicament.

To achieve the above objective, the present disclosure adopts the following technical solutions:

Use of baicalin in preparation of an anti-PRV medicament is provided.

In the anti-PRV medicament, a concentration of the baicalin used without causing a toxic effect on cells is 31.25-125 μM.

In the anti-PRV medicament, a concentration of the baicalin used for inhibiting PRV proliferation is 62.5-125 μM.

A medicament for inhibiting PRV replication and proliferation prepared by the baicalin is provided.

The medicament includes a pharmaceutical composition or compound preparation using the baicalin as an active pharmaceutical ingredient (API).

A concentration of the baicalin in the pharmaceutical composition or compound preparation is 62.5-125 μM.

The pharmaceutical composition or compound preparation further includes pharmaceutically acceptable excipients.

The present disclosure has the following beneficial effects:

The present disclosure discovers for the first time that baicalin has anti-PRV activity, and provides use of the baicalin in preparation of an anti-PRV pharmaceutical composition. Baicalin shows a significant inhibitory effect on PRV proliferation in host cells, and has an excellent anti-PRV effect.

In the examples of the present disclosure, porcine kidney epithelial cells (PK-15) are used as a cell model for research. Experimental results show that the baicalin has no obvious toxicity to cells in the using concentration range of 31.25-125 μM; the baicalin can significantly inhibit PRV proliferation in the concentration range of 62.5-125 μM, and the virus inhibitory effect is positively correlated with the using concentration of the baicalin. It can be foreseen that the baicalin can be developed as a safe and effective anti-PRV medicament, and a novel anti-PRV medicament under existing application conditions of the baicalin, with an excellent application prospect.

DETAILED DESCRIPTION

The specific implementation of the present disclosure will be described in further detail below in conjunction with the examples. Unless otherwise specified, all instruments and equipment in the examples are conventional; the related reagents are all commercially available conventional reagents; and the related test methods are all conventional methods.

Cells, viruses and main reagents used in the present disclosure are as follows:

Porcine kidney epithelial cells (PK-15 cells), PRV-GFP strain (PRV strain with green fluorescence), PRV-HeNLH/2017 strain (clinically isolated prevalent strain), and monoclonal antibody against PRV gE protein are all preserved by our laboratory. Baicalin (Cat. No.: Y0001273, Sigma-Aldrich), anti-β-tubulin mouse monoclonal antibody (Cat. No.: AT819, Beyotime Biotechnology), and Cell Counting Kit-8 (Cat. No.: CAT210, Solarbio Science & Technology (Beijing) Co., Ltd.) are used. All experiments related to live viruses were performed in biosafety level 2 facilities.

The baicalin is represented by the following structural formula:

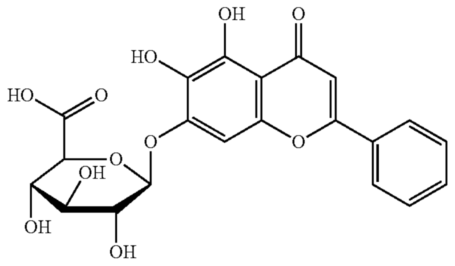

Example 1: Detection of Toxicity of Baicalin to PK-15 Cells

PK-15 cells were inoculated into a 96-well plate at $1\times10^4$ cells/well, and cultured in a constant temperature cell culture incubator at 37° C. and 5% $CO_2$ until the cell abundance reached 80%. Different concentrations of baicalin diluted with dimethyl sulfoxide (DMSO) were added (three replicates were set for each concentration): 0 (DMSO group), 31.25, 62.5, 125, 250, 500, and 1,000 μM, while an untreated Mock control group was set up. The cell culture plate was placed in the cell culture incubator to further incubate for 48 h, 10 μL of Cell Counting Kit-8 (CCK-8) reagent was added to each well, and the culture plate was placed in the cell incubator to further incubate for 2 h. Subsequently, the absorbance at 450 nm was detected using a multifunctional microplate reader. Data were analyzed using GraphPad 7.0 software, and Student's t test was used for statistical analysis. ns indicated no significant difference, and ***$P<0.001$ indicated extremely significant difference.

Figure 1:
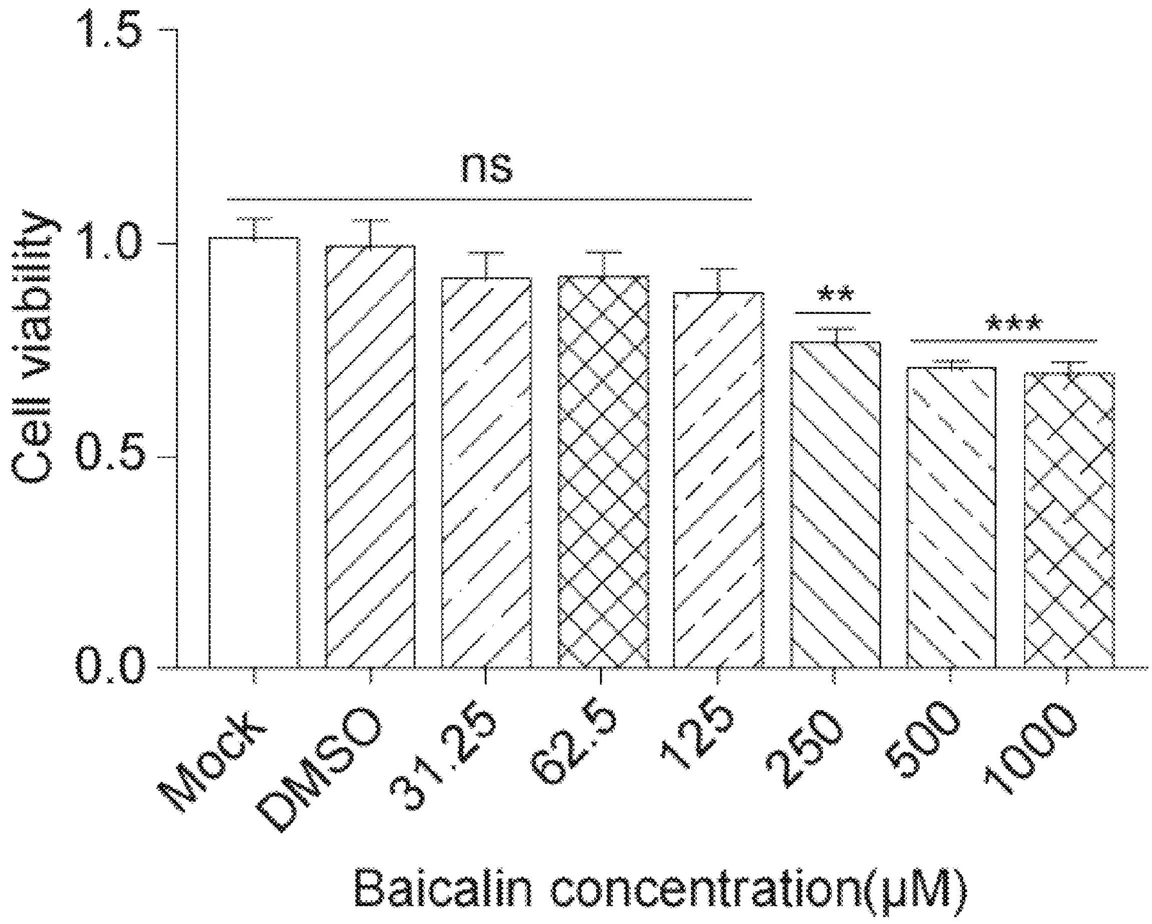
FIG. 1 illustrates detection of toxicity of baicalin to PK-15 cells.

The results are shown in FIG. 1. Compared with the blank control Mock group and the DMSO treatment group, baicalin had no significant effect on cell viability in the using concentration range of 31.25-125 μM, namely, the cytotoxicity of baicalin was small in this concentration range, with high biosafety.

Example 2: Detection of Anti-PRV Activity of Baicalin by Fluorometry

PK-15 cells were inoculated into a 96-well plate at $1\times10^4$ cells/well, and cultured in a constant temperature cell incubator at 37° C. and 5% $CO_2$ until the cell abundance reached 80%. Specified concentrations (31.25, 62.5, and 125 μM) of baicalin diluted with DMSO were added, while a DMSO control group (0 μM baicalin) was set up. After further incubation for 12 h, the cells were infected with the PRV-GFP strain with a multiplicity of infection of 0.1 (MOI=0.1), and incubated at 37° C. for 1.5 h. The viral supernatant was discarded, the cells were rinsed with PBS three times, and DMEM maintenance medium supplemented with the corresponding concentration of baicalin was added for further culturing for 24 h. Subsequently, the culture medium was discarded, the cells were rinsed with phosphate buffered saline (PBS) three times, and 50 μL of 4% (m/v) paraformaldehyde was added to each well and let stand to fix at room temperature for approximately 20 min. After rinsing with PBS three times, the 96-well plate was observed under a fluorescence microscope. The green fluorescence intensity represented the proliferation of PRV strains.

Figure 2:
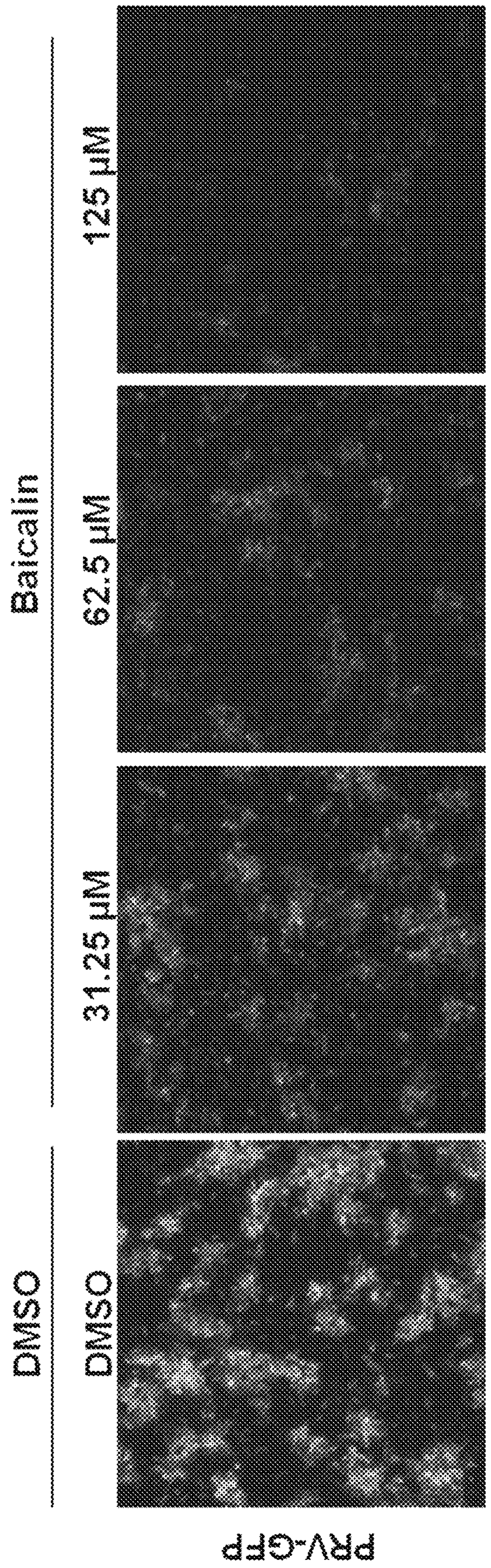
FIG. 2 illustrates detection of anti-PRV activity of baicalin by fluorometry (×100 μm).

The results are shown in FIG. 2. Compared with the DMSO control group, baicalin inhibited the proliferation of PRV-GFP strains at the using concentrations, and the inhibitory effect was more significant at 62.5 and 125 μM, namely, baicalin had excellent anti-PRV activity at these concentrations.

Example 3: Detection of the Inhibitory Effect of Baicalin on Expression of PRV gE Protein by Western Blot In order to further confirm the anti-PRV activity of baicalin, the inhibitory effect of baicalin on the expression of gE, the main structural protein of PRV, was detected by Western blot. The specific method was as follows:

PK-15 cells were inoculated into a 24-well cell culture plate at $2.5\times10^5$ cells/well. When the cells grew to an abundance of approximately 70%, specified concentrations (62.5 and 125 μM) of baicalin diluted with DMSO were added, while a DMSO control group (0 μM baicalin) and an untreated Mock control group were set up. After further incubation for 12 h, the cells were infected with PRV-HeNLH/2017 strain (a clinically isolated prevalent strain) with MOI=0.1 and incubated for 1.5 h. The culture medium was discarded, and the cells were rinsed with PBS for three times; 500 μL of maintenance medium supplemented with the corresponding concentration of baicalin was added, and the cell culture plate was put in the cell incubator for further culturing for 24 h; the cells were lysed by repeated freezing and thawing three times, the freeze-thaw lysate was transferred to a 1.5 mL sterile centrifuge tube and centrifuged at 12,000 rpm for 3 min; the supernatant was transferred to a new 1.5 mL sterile centrifuge tube, namely, the samples of the DMSO control group and the baicalin treatment group were prepared. Subsequently, anti-gE (anti-PRV gE protein antibody, upper panel in FIG. 3) and anti-β-tubulin (anti-tubulin antibody, lower panel in FIG. 3) mouse monoclonal antibodies were used to detect the expression of PRV gE protein and cell reference protein 0-tubulin by Western blot.

Figure 3:
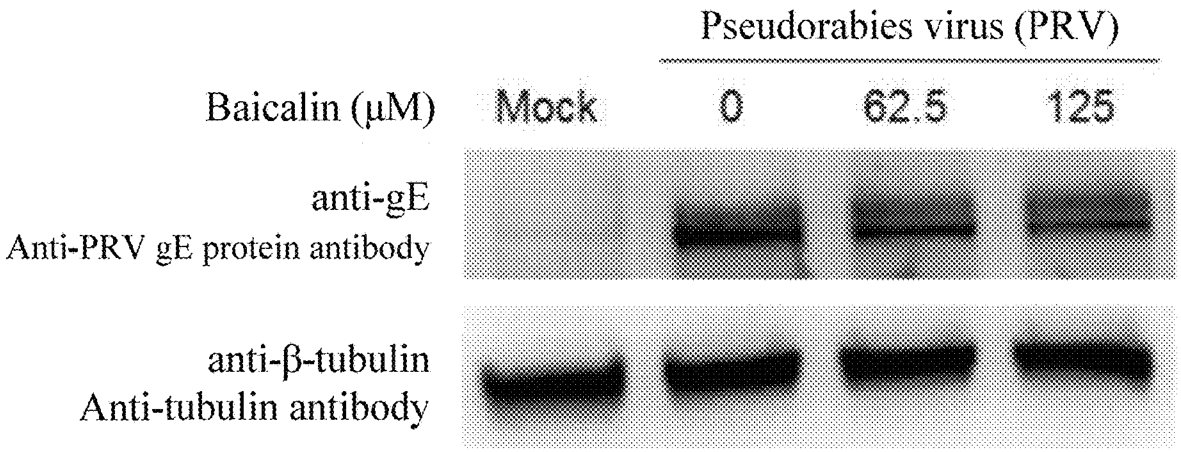
FIG. 3 illustrates detection of an inhibitory effect of baicalin on expression of PRV gE protein by Western blot.

The results are shown in FIG. 3. Compared with the Mock control group and the DMSO treatment group, baicalin significantly inhibited the expression of PRV gE protein at 62.5 and 125 μM.

Example 4: The Inhibitory Effect of Baicalin on PRV Proliferation In Vitro

PRV titer was measured by using 50% tissue culture infectious dose ($TCID_{50}$) to further evaluate the inhibitory effect of baicalin on PRV progeny viruses. The specific method was as follows:

PK-15 cells were inoculated into a 24-well plate at $2.5\times10^5$ cells/well, and cultured in a cell incubator until the cell abundance reached around 70%. Specified concentrations (62.5 and 125 μM) of baicalin diluted with DMSO were added, while a DMSO control group (0 μM baicalin)

was set up. Three replicate wells were set up for each group. After further incubation for 6 h, the cells were infected with the PRV-HeNLH/2017 strain (a clinically isolated prevalent strain) with MOI=0.1, and incubated at for 1.5 h. The culture medium was discarded, the cells were rinsed with PBS three times, and 500 μL of DMEM maintenance medium supplemented with the corresponding concentration of baicalin was added for culturing for 12, 24, and 36 h, respectively. Under aseptic conditions, for each group, 50 μL of cell culture supernatant was cryopreserved in a freezer at −80° C. for later use.

The determination of the PRV titer in the cell culture supernatant was carried out according to the following steps: PK-15 cells were plated on a 96-well cell culture plate at $1.0\times10^4$ cells/well. When the cells grew to around 70% abundance, the above collected cell culture supernatant samples of the DMSO control group and the baicalin treatment group were diluted 10-fold with DMEM supplemented with 2% (v/v) fetal bovine serum (FBS), and inoculated with PK-15 cells (100 μL per well) plated on the 96-well cell culture plate; 8 replicates were made for each dilution. Meanwhile, a sample-free normal cell control group was set up. The cell culture plate was cultured in a cell incubator. The cell growth was observed every 24 h and the number of cytopathic wells was recorded. The observation lasted for 3-5 days until the number of cytopathic wells no longer increased; the $TCID_{50}$ of the virus was calculated by the Reed-Muench method. Statistical analysis was performed using GraphPad 7.0 software, and Student's t test was used for statistical analysis of data. ***$P<0.001$ indicated a very significant statistical difference.

Figure 4:
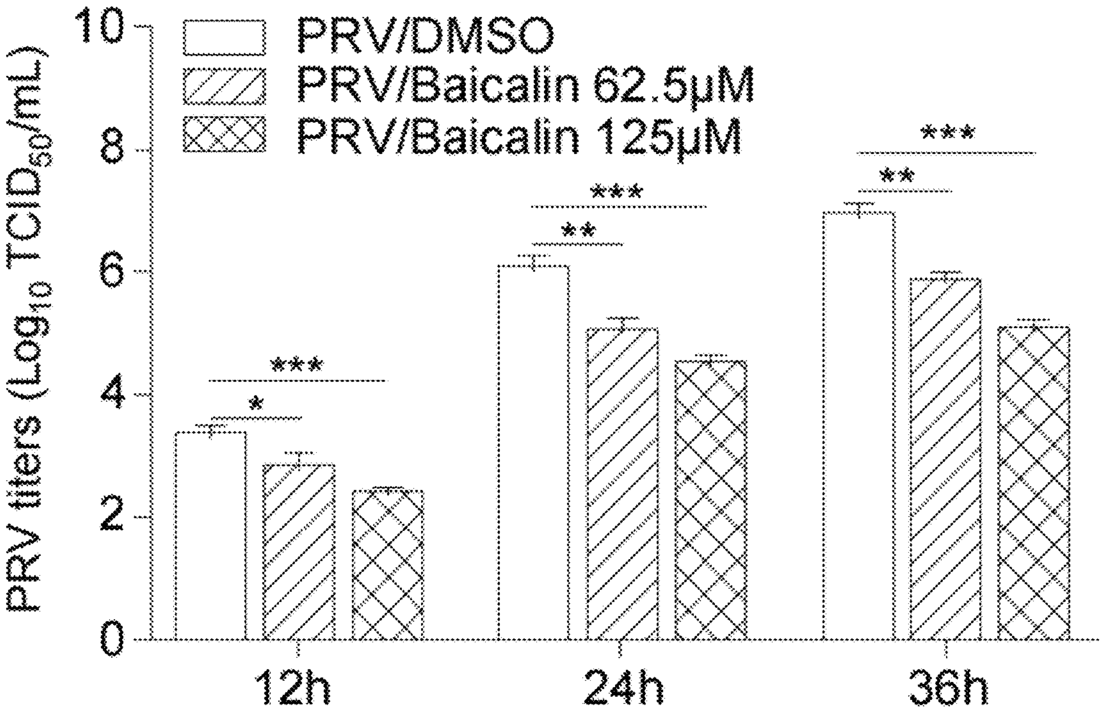
FIG. 4 illustrates an inhibitory effect of baicalin on PRV proliferation in vitro.

The results are shown in FIG. 4. Compared with the DMSO control group, the baicalin treatment group significantly inhibited the proliferation of PRV on PK-15 cells, and the inhibitory effect was positively correlated with the concentration of baicalin, namely, the baicalin had an excellent inhibitory effect on PRV proliferation in vitro.

What is claimed is:

1. A method of treating pseudorabies virus (PRV) infection, comprising administering an anti-PRV medicament to a subject in need thereof;

wherein the anti-PRV medicament comprises an active pharmaceutical ingredient (API), and the API consists of baicalin; and wherein a concentration of baicalin in the anti-PRV medicament, used without causing a toxic effect on cells, is 31.25 μM-125 μM.

2. The method according to claim 1, wherein in the anti-PRV medicament, a concentration of the baicalin used for inhibiting PRV proliferation is 62.5 μM-125 μM.

* * * * *